(12) United States Patent
Blase et al.

(10) Patent No.: US 9,999,435 B2
(45) Date of Patent: Jun. 19, 2018

(54) ENDOSCOPIC INSTRUMENT

(71) Applicant: Karl Storz SE & Co. KG, Tuttlingen (DE)

(72) Inventors: Bastian Blase, Berlin (DE); Sebastian Röthig, Berlin (DE); Sebastian Schlegel, Berlin (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 296 days.

(21) Appl. No.: 14/795,472

(22) Filed: Jul. 9, 2015

(65) Prior Publication Data

US 2016/0008018 A1    Jan. 14, 2016

(30) Foreign Application Priority Data

Jul. 10, 2014    (DE) .................. 10 2014 109 663

(51) Int. Cl.
*A61B 17/00* (2006.01)
*A61B 17/29* (2006.01)
(Continued)

(52) U.S. Cl.
CPC ...... *A61B 17/29* (2013.01); *A61B 2017/0034* (2013.01); *A61B 2017/00296* (2013.01);
(Continued)

(58) Field of Classification Search
CPC .................. A61B 17/29; A61B 17/282; A61B 2017/2927; A61B 2017/2929;
(Continued)

(56) References Cited

U.S. PATENT DOCUMENTS 7,686,826 B2    3/2010    Lee et al.
8,574,243 B2    11/2013    Saadat et al.
(Continued)

FOREIGN PATENT DOCUMENTS

CA        2663305            3/2008
DE    102006028001 A1    12/2007
(Continued)

OTHER PUBLICATIONS

European Search Report Application No. EP 15176133.5 Completed: Sep. 14, 2015; dated Sep. 22, 2015 8 pages.

*Primary Examiner* — Tuan V Nguyen
(74) *Attorney, Agent, or Firm* — Whitmyer IP Group LLC

(57) ABSTRACT

Endoscopic instrument having a shaft extending between a proximal end and a distal end along a longitudinal direction, wherein a working section on the distal end and an actuating element on the proximal end are operatively connected by a thrust element extending along the longitudinal direction, wherein the working section has a jaw piece with first and second jaw parts, which jaw piece is arranged pivotably on a jaw part holder, which is arranged in the shaft so as to be displaceable along the longitudinal direction and rotatable about the longitudinal direction and the thrust element is coupled to the jaw piece, wherein the jaw piece, in the closed state, can be retracted into the shaft, and a blocking device is provided in the instrument which is configured to block a retraction of the jaw piece into the shaft in a predefined angle range about the longitudinal direction.

17 Claims, 16 Drawing Sheets

(51) Int. Cl.
    *A61B 90/00* (2016.01)
    *A61B 34/30* (2016.01)
(52) U.S. Cl.
    CPC ........... *A61B 2017/00353* (2013.01); *A61B 2017/293* (2013.01); *A61B 2017/2906* (2013.01); *A61B 2017/2927* (2013.01); *A61B 2017/2929* (2013.01); *A61B 2017/2932* (2013.01); *A61B 2017/2946* (2013.01); *A61B 2034/305* (2016.02); *A61B 2090/034* (2016.02); *A61B 2090/0801* (2016.02)
(58) Field of Classification Search
    CPC .... A61B 2017/2936; A61B 2017/2939; A61B 2017/2944; A61B 2017/2946; A61B 2017/2906
    See application file for complete search history.

(56) References Cited

U.S. PATENT DOCUMENTS

2003/0065358 A1* 4/2003 Frecker .............. A61B 17/29
                                                606/205
2007/0078459 A1* 4/2007 Johnson ............. A61B 17/29
                                                606/51
2007/0283970 A1  12/2007 Mohr et al.
2008/0065116 A1   3/2008 Lee et al.
2009/0259248 A1  10/2009 Ganter et al.
2010/0081874 A1*  4/2010 Miyamoto ......... A61B 1/00087
                                                600/109
2011/0160532 A1*  6/2011 Heimberger ....... A61B 1/00073
                                                600/106
2011/0196407 A1   8/2011 BenMaamer
2015/0119918 A1   4/2015 Blase et al.

FOREIGN PATENT DOCUMENTS

| | | |
|---|---|---|
| EP | 1946704 B1 | 7/2008 |
| EP | 2322076 A1 | 5/2011 |
| EP | 2752166 A2 | 7/2014 |
| WO | 2007144172 A | 12/2007 |
| WO | 2014006186 A1 | 1/2014 |

* cited by examiner

ENDOSCOPIC INSTRUMENT

CROSS-REFERENCES TO RELATED APPLICATIONS

This application claims priority from German patent application 10 2014 109 663.0, filed on Jul. 10, 2014. The entire contents of this priority application is incorporated herein by reference.

BACKGROUND

The present disclosure relates to an endoscopic instrument having a shaft which extends between a proximal end of the instrument and a distal end of the instrument along a longitudinal direction, wherein a working section is arranged on the distal end and an actuating element is arranged on the proximal end, which actuating element permits an actuation of the working section, wherein the working section and the actuating element are operatively connected by a thrust element which extends along the longitudinal direction, and wherein the working section has a jaw piece with a first jaw part and a second jaw part, which jaw piece is arranged pivotably on a jaw part holder.

In recent years, the number of surgical procedures performed using endoscopic operation techniques has increased ever further. This is firstly owing to the fact that an ever greater number of operation techniques have been developed which make it possible to perform a less traumatic procedure on the patient than is possible using conventional operation techniques. It is however also the case that ever more refined endoscopic instruments have been developed which, owing to a smaller diameter, cause less trauma to the patient and provide the user with greater freedom during the operation when the endoscopic instrument is in the body of the patient.

Despite these developments, difficulties still exist in providing an endoscopic instrument which has as small a diameter as possible and whose working section at the distal end of the instrument nevertheless provides the user with greater positioning freedom and mobility. Here, it would be expedient in particular if multiple working sections could be implemented in one endoscopic instrument, as this would eliminate the need for a changeover of the endoscopic instrument or the insertion of multiple endoscopic instruments.

Examples of endoscopic instruments which seek to permit great positioning freedom and mobility are presented in the documents U.S. Pat. No. 7,686,826, CA 2 663 305 and US 2007/0283970.

SUMMARY

It is therefore an object to specify an improved endoscopic instrument. Here, the improved instrument should, while having a small shaft diameter, provide the user with greater freedom with regard to the actuation of a working section at the distal end of the endoscopic instrument.

There is provided an endoscopic instrument having a shaft which extends between a proximal end of the instrument and a distal end of the instrument along a longitudinal direction, wherein a working section is arranged on the distal end and an actuating element is arranged on the proximal end, which actuating element permits an actuation of the working section, wherein the working section and the actuating element are operatively connected by a thrust element which extends along the longitudinal direction, wherein the working section has a jaw piece with a first jaw part and a second jaw part, which jaw piece is arranged pivotably on a jaw part holder, wherein the jaw part holder is arranged in the shaft so as to be displaceable along the longitudinal direction and rotatable about the longitudinal direction and the thrust element is coupled to the jaw piece, wherein the jaw piece is configured such that, in the closed state, it can be retracted into the shaft, wherein, in the instrument, there is provided a blocking device which is configured to block a retraction of the jaw piece into the shaft in a predefined angle range about the longitudinal direction.

Using a single thrust element it may be possible for the jaw piece to be deployed out of the shaft into a working position, for the jaw piece to be opened and closed, for the jaw piece to be rotated about the longitudinal direction, and for the jaw piece to be retracted into the shaft into a rest position. It may duly also be possible for these various functions to be controlled by way of two or more thrust elements, but the use of precisely one thrust element may yield a particularly small diameter of the endoscopic instrument.

Using the blocking device, it may be possible to influence whether an actuation of the thrust element should effect an opening or closing of the jaw part or should effect a retraction or deployment of the jaw part relative to the shaft. This may be achieved in that, in a first state, the blocking device prevents a retraction of the jaw piece into the shaft, and in a second state, the blocking device permits a retraction of the jaw piece into the shaft.

In a further refinement, the functionality is specifically as follows: when the blocking device is in the first state and the thrust element is subjected to a pulling force, that is to say a force in the direction of the proximal end of the endoscopic instrument, said pulling action cannot cause the jaw piece to be retracted into the shaft because the blocking device blocks the retraction. Instead, the force acts on the jaw piece and leads to an actuation of the jaw piece. In a further refinement, a pulling action on the thrust element causes a closure of the jaw piece.

By contrast, if the blocking device is in the second state, a pulling action on the thrust element has the effect that the jaw piece is retracted into the shaft. Here, in a further embodiment, the jaw piece is configured such that it is closed when retracted into the shaft. By contrast, another further embodiment requires that the jaw piece be closed by the user beforehand. For this purpose, the jaw piece is then configured such that it itself blocks a retraction of the jaw piece in the open state. For a retraction of the jaw piece, it is necessary in this case for the jaw piece to initially be closed and for the blocking device to then be transferred into the second state, if this has not already been done.

The transfer of the blocking device from the first state into the second state or from the second state into the first state is however, according to an exemplary embodiment, effected by way of a rotation of the thrust element. It may duly also be possible for the adjustment of the blocking device to be realized by way of an additional control element. However, with regard to a small diameter of the endoscopic instrument, according to an exemplary embodiment, the adjustment may be performed by an existing element, in this case the thrust element.

In a further refinement, the user rotates the thrust element—and thus also the jaw piece—into a particular angular position. Said angular position is dependent on whether the user wishes to block or enable the retraction of the jaw piece. In other words, if the user rotates the jaw piece into an angular position situated in the predefined angle range, the retraction of the jaw piece into the shaft is blocked. If the user rotates the jaw piece into an angular position which lies outside the predefined angle range, the retraction of the jaw piece into the shaft is permitted.

In a further refinement, precisely one continuous angle range is provided in which the blocking device blocks the retraction of the jaw piece. In other further refinements, two or more angle ranges are provided in which the blocking device blocks the retraction of the jaw piece. Here, according to an exemplary embodiment, the angle range or the sum of the angle ranges in which the retraction is blocked may be greater than the remaining angle ranges in which the retraction is possible.

In a further refinement, there is no direct mechanical operative connection between the thrust element and the jaw part holder. In particular, no forces are transmitted directly from the thrust element to the jaw part holder. Instead, in a further refinement, forces may be transmitted from the thrust element to the jaw part holder via the jaw piece.

This may make it possible for a force transmitted via the thrust element to be conducted firstly to the jaw piece. If the jaw piece can absorb the force for an opening or closing movement of the jaw piece, the jaw part holder can remain substantially stationary. By contrast, if the jaw piece cannot convert the force into a movement, for example because the jaw piece is closed, the force can be transmitted onward to the jaw part holder and, for example in a manner dependent on the state of the blocking device, effect a retraction of the jaw piece.

It is pointed out that the expression "thrust" encompasses both positive thrust and negative thrust, that is to say a pulling action. The thrust element thus transmits both a thrust action and a pulling action. Furthermore, it is pointed out that the expression "pivoting of the jaw piece" encompasses in particular an opening and closing of the jaw piece.

In a refinement, the blocking device has a first blocking element which is arranged positionally fixedly relative to the shaft, and the blocking device has a second blocking element, which is arranged positionally fixedly relative to the jaw part holder, wherein, according to an exemplary embodiment, the first blocking element is in the form of a groove, and the second blocking element is in the form of a projection.

This refinement may be interesting from a manufacturing aspect. It may furthermore be possible for the diameter of the endoscopic instrument to be kept small. If the first blocking element and the second blocking element block one another with regard to the longitudinal direction, that is to say with regard to a thrust action or pulling action on the thrust element, the movement of the jaw part holder relative to the shaft is thus also blocked. If the first blocking element can be displaced relative to the second blocking element in a longitudinal direction, it may thus also be possible for the jaw part holder to be displaced relative to the shaft, and a retraction of the jaw piece into the shaft may be possible. On the basis of the exemplary embodiments, it will be clarified further how the use of a groove as a first blocking element and of a projection as a second blocking element can be implemented to realize the blocking device. It is however pointed out at this juncture that a structurally reversed situation may basically also be possible, that is to say in which the first blocking element may be in the form of a projection and the second blocking element may be in the form of a groove, because the mutual blocking of the first and second blocking element in a longitudinal direction is sought, and not the specific manner in which the blocking is effected.

In a further refinement, the blocking device has a longitudinal groove, which is formed in the shaft along the longitudinal direction, and has a projection, which is arranged on the jaw part holder and which is guided in the longitudinal groove during a displacement of the jaw part holder along the longitudinal direction.

This refinement may permit a simple construction of the blocking device. In this case, the longitudinal groove can be of very short form with respect to the longitudinal direction of the endoscopic instrument. In a further refinement, the longitudinal groove may have the function of realizing that a retraction of the jaw piece into the shaft is possible only when the projection enters the longitudinal groove. In other words, a retraction of the jaw piece into the shaft may be possible only when the projection on the jaw part holder is introduced into the longitudinal groove when a pulling action is exerted on the thrust element. If the projection fails to enter the longitudinal groove, that is to say the end side of the longitudinal groove, the projection prevents a retraction of the jaw piece.

In a further refinement, on the distal end of the shaft, there is formed an annular groove into which the projection arranged on the jaw part holder can enter, such that the jaw part holder can be rotated about the longitudinal direction when the projection has entered the annular groove.

This refinement may make it possible for the jaw piece to be rotated about the longitudinal direction at least when the projection has entered the annular groove. Here, according to an exemplary embodiment, the annular groove has an opening on a side facing toward the proximal end of the instrument. Then, when the projection, during its rotation, comes to be situated in front of said opening, it may be possible, by the exertion of a pulling action on the thrust element, for the jaw part holder with the projection to be pulled in the direction of the proximal end, and thus for the jaw piece to be retracted. The angle range in which the opening is not arranged is then the abovementioned angle range in which a retraction of the jaw piece is blocked. In a further refinement, the opening in the annular groove forms the start of a longitudinal groove, in particular of a longitudinal groove as described above.

In a further refinement, the blocking device has a longitudinal groove, which is formed in the shaft along the longitudinal direction, the blocking device has an annular groove on the distal end of the shaft, and the blocking device has a projection, which is arranged on the jaw part holder, wherein the projection is guided in the longitudinal groove and in the annular groove.

This refinement may make it possible for the blocking device to be realized in a simple manner in terms of construction. In this case, the longitudinal groove opens into an annular groove, such that the projection can be transferred from the longitudinal groove into the annular groove and from the annular groove into the longitudinal groove. For as long as the projection is situated in the annular groove, the jaw part holder can be rotated with the jaw piece about the longitudinal direction. If the projection is situated at a location along the circumferential extent of the annular groove which does not coincide with the transition of the longitudinal groove into the annular groove, the projection blocks a movement of the jaw part holder in the longitudinal direction. This means that the jaw piece closes when a pulling action is exerted on the thrust element and opens when a thrust action is exerted on the thrust element. If the projection is situated at a position in which the longitudinal groove opens into the annular groove, a pulling action on the thrust element leads to a retraction of the jaw piece. The projection is not guided simultaneously in the longitudinal groove and in the annular groove.

In a further refinement, the first jaw part and the second jaw part are pivotable about a common first axis and the jaw piece is coupled to the thrust element at a second axis, wherein the first axis and the second axis are spaced apart from one another, and in particular, the first axis is situated further distally than the second axis.

This refinement may permit a structurally interesting design of the jaw piece. In particular, it can be achieved that forces high enough for a working process or working step can be applied to the jaw piece.

In a further refinement, the first jaw part is coupled to the thrust element by way of a first articulated connection and/or the second jaw part is coupled to the thrust element by way of a second articulated connection.

This refinement may make it possible, even in the case of spatially small dimensions, for the jaw piece to be opened adequately widely and closed with adequate force.

In a further refinement, on the distal end of the shaft, there is formed a stop which delimits a displacement of the jaw part holder along the longitudinal direction at the distal side.

This refinement can have the effect that, when a thrust action is exerted on the thrust element, the jaw piece is deployed from the shaft in the substantially closed state, and opens only when the jaw part holder abuts against the stop. This may make it possible, in a particularly effective manner, for the user to control the displacement of the jaw piece and the opening thereof in succession, even if the displacement and opening of the jaw piece are performed by way of a single thrust element. When the jaw part holder can be displaced no further distally, the force transmitted to the thrust element by the thrust action is transmitted to the jaw piece, which then opens.

In a further refinement, the thrust element is displaceable along the longitudinal direction relative to the jaw part holder at least when the jaw piece has been deployed out of the shaft.

This refinement may make it possible for the opening and closing of the jaw piece to be effected by way of the thrust element in a structurally simple manner.

In a further refinement, the thrust element, when subjected to thrust toward the distal end, exerts on the jaw piece a force which can open the jaw piece, and the shaft is configured, in spatial terms, such that an opening of the jaw piece in the shaft is prevented.

This refinement may make it possible to realize that, although the thrust element interacts primarily with the jaw piece, the action is transmitted from the jaw piece to the jaw part holder if the jaw piece cannot open. A thrust action on the thrust element primarily causes a force to act which can open the jaw piece. However, if the jaw piece, in the shaft, is prevented from opening, said force is transmitted to the jaw part holder on which the jaw piece is pivotably arranged. This in turn has the effect that the thrust action on the thrust element then acts on the jaw part holder and displaces the jaw part holder in the shaft.

In a further refinement, the thrust element has an elongate thrust shaft which is guided displaceably in a sleeve of the jaw part holder, wherein the sleeve is guided in a channel in the interior of the shaft.

This refinement may permit a good transmission of a pulling action or a thrust action by the thrust element, even if the shaft of the endoscopic instrument is long and/or the diameter of the shaft is small.

In a further refinement, the shaft has, at the distal end, a region which can be angularly deflected, and the angular deflection is controlled by an angular-deflection control element which can be actuated from the proximal end of the instrument.

This refinement provides a further degree of freedom for the displacement of the jaw piece.

In a further refinement, a working process can be performed using two working sections, wherein a second actuating element is arranged on the proximal end, which second actuating element permits an actuation of the second working section, wherein the second working section and the second actuating element are operatively connected by way of a second thrust element which extends along the longitudinal direction, wherein the second working section has a second jaw piece with a third jaw part and with a fourth jaw part, which second jaw piece is pivotably arranged on a second jaw part holder, wherein the second jaw part holder is arranged in the shaft so as to be displaceable along the longitudinal direction and rotatable about the longitudinal direction, and the second thrust element is coupled to the second jaw piece, wherein the second jaw piece is configured such that, in the closed state, it can be retracted into the shaft, wherein, within the instrument, there is arranged a second blocking device which is configured to block a retraction of the second jaw piece into the shaft in a second angle range about the longitudinal direction.

This refinement may make it possible to perform work using two or more working sections, wherein the configuration may be selected as required such that, at all times, work is performed using only one deployed working section, or two or more working sections can be deployed simultaneously, and it may also be possible for work to be performed using two or more working sections simultaneously. It may be also possible for use to be made of further working sections which do not have a jaw piece.

In a further refinement, the shaft has, on the distal end, an opening slot into which a projection of the blocking device can enter during a rotation about the longitudinal direction.

As will be presented on the basis of an exemplary embodiment, this refinement may make it possible to realize a small diameter of the shaft of the endoscopic instrument.

In a further refinement, the angle range is at least 180°, according to an exemplary embodiment at least 270°, according to another exemplary embodiment at least 315°, according to yet another exemplary embodiment at least 300°, and according to yet a further exemplary embodiment at least 335°.

This refinement may make it possible, in a manner dependent on the desired configuration of the operation of the endoscopic instrument, that, firstly, an adequately large range for an actuation of the jaw piece is realized, and secondly, the jaw piece can be retracted easily and reliably.

BRIEF DESCRIPTION OF THE DRAWINGS

It is self-evident that the features mentioned above and the features yet to be discussed below can be used not only in the respectively specified combination but also in other combinations or individually without departing from the scope of the present disclosure.

Exemplary embodiments are illustrated in more detail in the drawing and will be discussed in more detail in the following description, in which.

DESCRIPTION OF EXEMPLARY EMBODIMENTS

Figure 1:
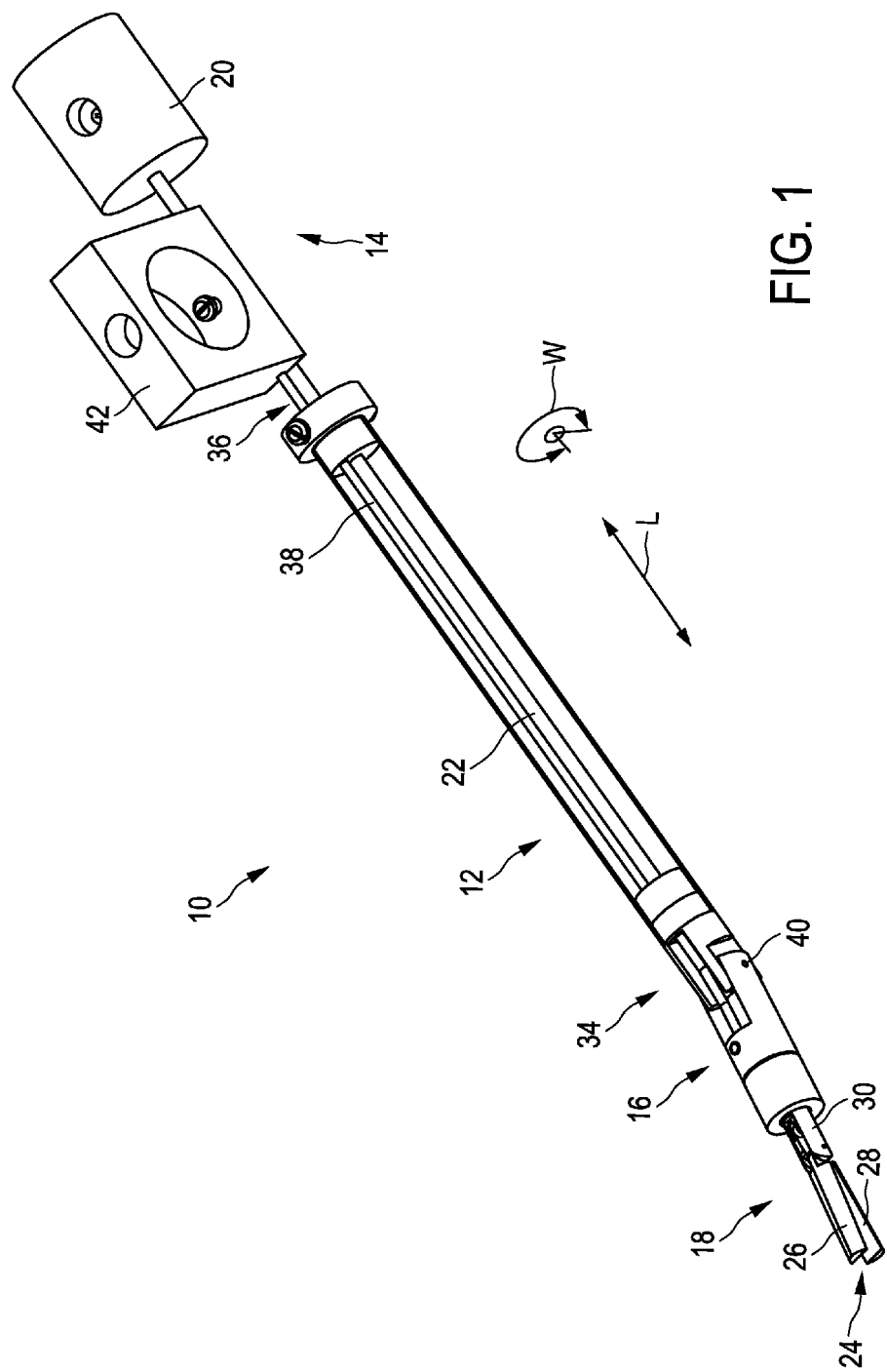
FIG. 1 shows a first embodiment of an endoscopic instrument.

FIG. 1 shows an endoscopic instrument 10 having a shaft 12 which extends between a proximal end 14 of the instrument 10 and a distal end 16 of the instrument 10 along a longitudinal direction L. A working section 18 is arranged on the distal end 16, and a symbolically indicated actuating element 20 is arranged on the proximal end 14. The actuating element 20 permits an actuation of the working section 18.

The working section 18 and the actuating element 20 are operatively connected by a thrust element 22 which extends along the longitudinal direction L.

The working section 18 has a jaw piece 24 with a first jaw part 26 and a second jaw part 28. The jaw piece 24 is arranged pivotably on a jaw part holder 30. The jaw part holder 30 is arranged in the shaft 12 so as to be displaceable along the longitudinal direction L and rotatable about the longitudinal direction L. The thrust element 22 is coupled to the jaw piece 24. The jaw piece 24 is configured such that, in the closed state, it can be retracted into the shaft 12.

In the instrument 10, there is arranged a blocking device 32 (see FIG. 4), which in this case is concealed by the shaft 12. The blocking device 32 is configured to block a retraction of the jaw piece 24 into the shaft 12 in a predefined angle range W about the longitudinal direction L.

The shaft 12 has, at the distal end 16, a region 34 which can be angularly deflected. The angular deflection of the region 34 is controlled by an angular-deflection control element 36 which can be actuated from the proximal end 14 of the instrument 10. In a further refinement which is not shown here, an angular-deflection unit as per WO 2014/006186 A1 is used, the document incorporated by reference in its entirety.

In this case, the angular-deflection control element 36 has an angular-deflection bar 38 which, at least in the vicinity of the uniaxial joint 40, is of flexible form. It may however basically also be possible for the entire angular-deflection bar to be of flexible form and to be stiffened in segments by way of thin casing tubes. For the exertion of a thrust action or a pulling action on the angular-deflection bar 38, a symbolically illustrated handle 42 is arranged on the proximal end 14.

Figure 2:
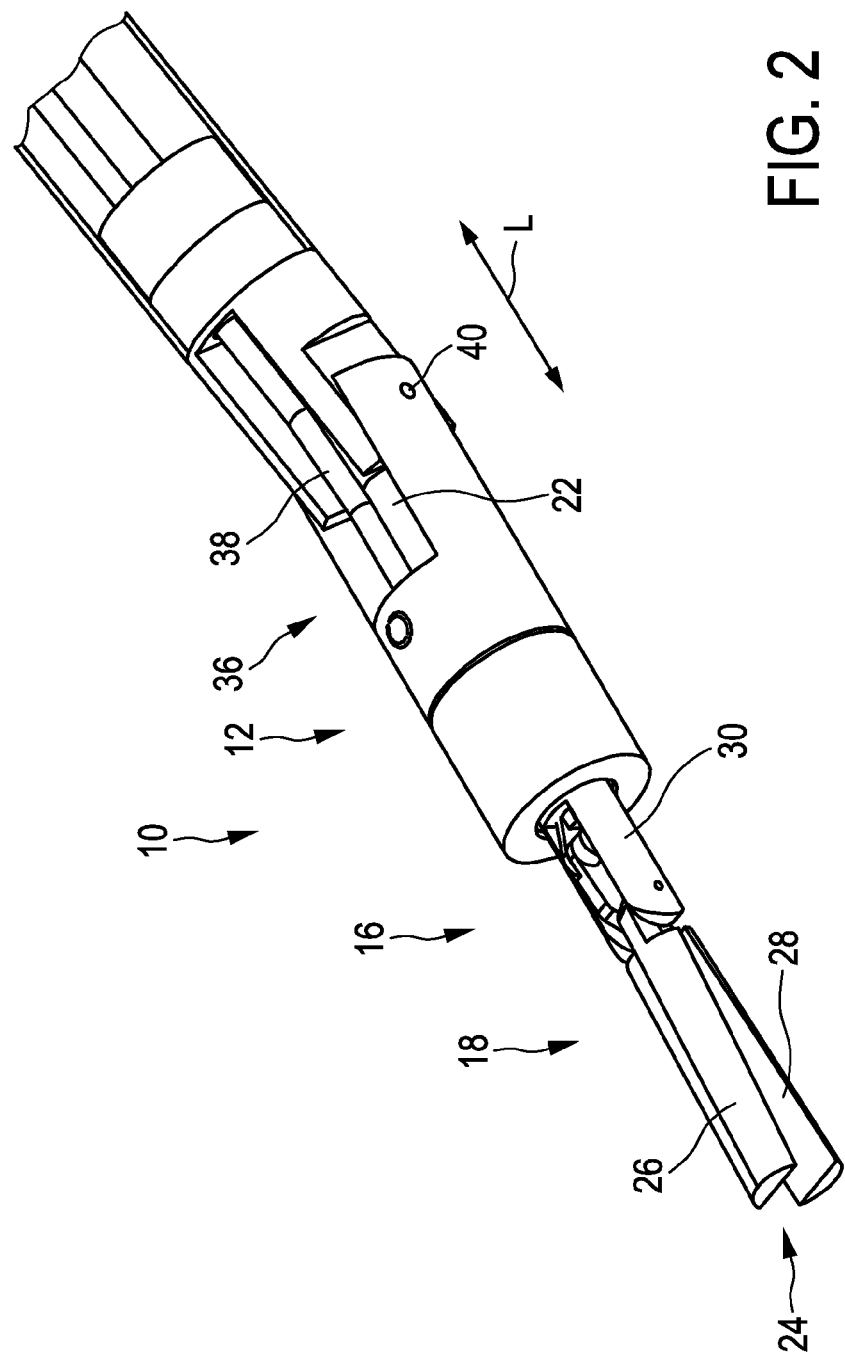
FIG. 2 shows an enlarged view of the distal end of the endoscopic instrument as per FIG. 1.

FIG. 2 shows an enlarged view of the distal end of the endoscopic instrument 10 from FIG. 1. Here, and below, reference signs that have already been introduced will also be used in the further figures to denote elements of identical function or at least similar function.

Figure 3:
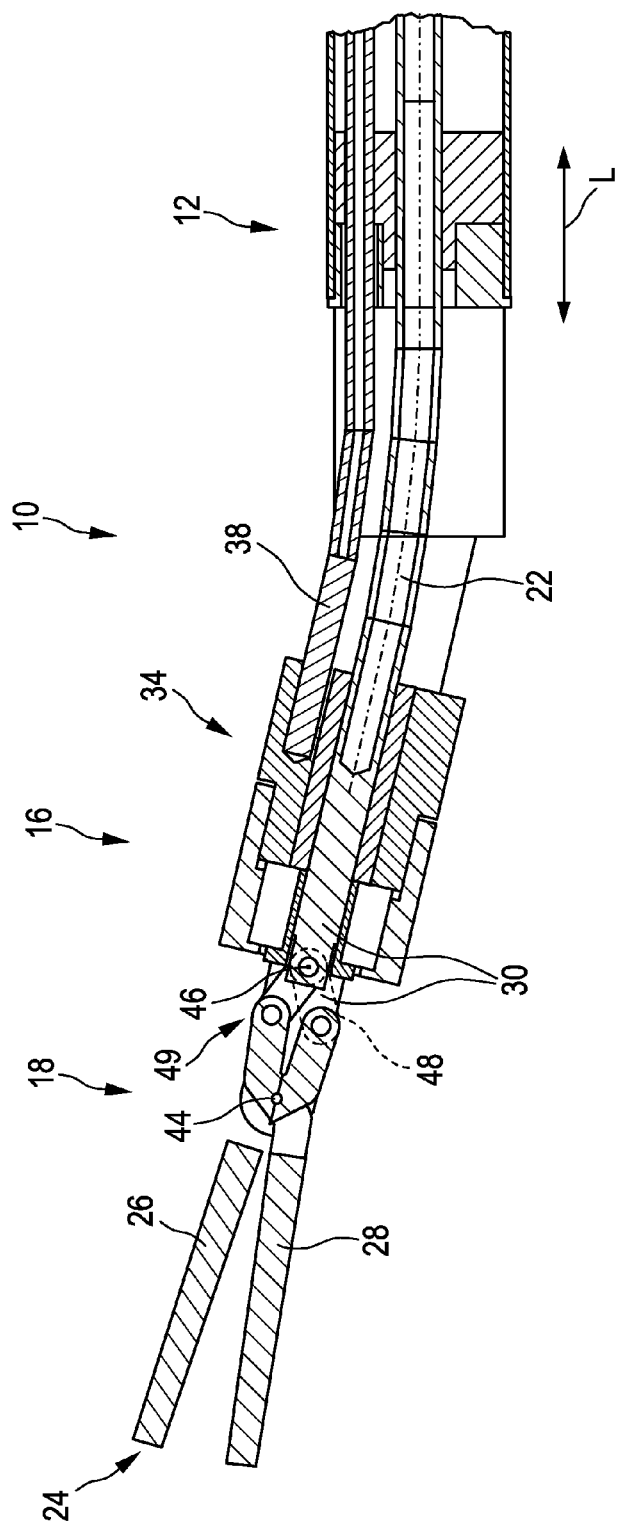
FIG. 3 shows a section through the distal part as per FIG. 2.

FIG. 3 shows a sectional view through the distal part of the instrument 10 as per FIG. 2. The sectional view is simplified and shows only the components that are visible in FIG. 2.

The first jaw part 26 and the second jaw part 28 are pivotable about a common first axis 44. The jaw part 24 is coupled to the thrust element 22 at a second axis 46, wherein the first axis 44 and the second axis 46 are spaced apart from one another. In this embodiment, the first axis 44 is situated further distally than the second axis 46. The first jaw part 26 is coupled to the thrust element 22 by way of a first articulated connection 48 (shown by way of dashed lines), and the second jaw part 28 is coupled to the thrust element 22 by way of a second articulated connection 49.

Figure 4:
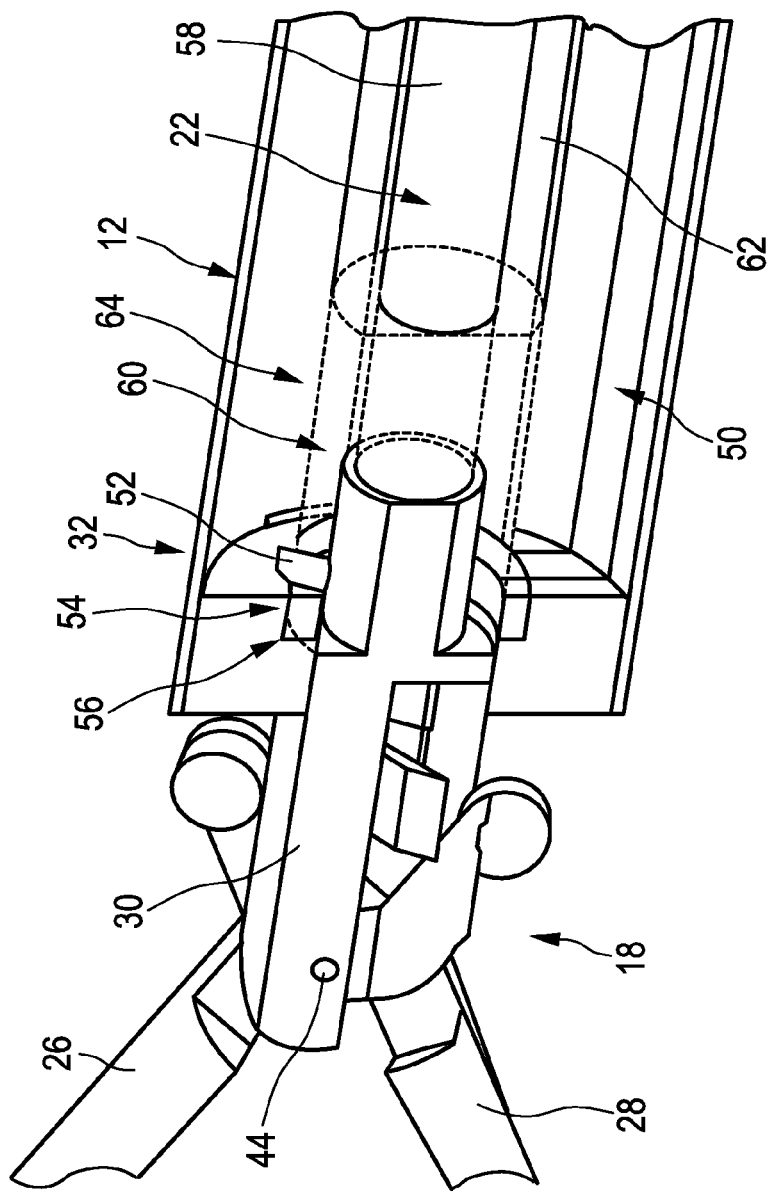
FIG. 4 shows an enlarged, partially sectional view into the interior of the distal part of the endoscopic instrument.

FIG. 4 shows, in a sectional view, an enlarged detail of the distal part of the endoscopic instrument 10. The components are illustrated, in part, in transparent form in order to give a better understanding of this embodiment.

The figure shows the blocking device 32. The blocking device 32 has a first blocking element, which is arranged positionally fixedly relative to the shaft 12 and which in this case is in the form of a longitudinal groove 50. The blocking device 32 furthermore has a second blocking element, which is arranged positionally fixedly relative to the jaw part holder 30 and which in this case is in the form of a projection 52.

On the distal end of the shaft 12, there is formed an annular groove 54 into which the projection 52 arranged on the jaw part holder 30 can enter, such that the jaw part holder 30 can be rotated about the longitudinal direction L when the projection 52 has entered the annular groove 54. The longitudinal groove 50 opens into the annular groove 54.

On the distal end of the shaft 12, there is formed a stop 56 which delimits a displacement of the jaw part holder 30 along the longitudinal direction L at the distal side. The thrust element 22 is displaceable along the longitudinal direction L relative to the jaw part holder 30 at least when the jaw piece 24 has, as shown, been deployed out of the shaft 12. In this exemplary embodiment, the stop 56 is the distal side wall of the annular groove 54.

The thrust element 22 has an elongate thrust shaft 58 which is guided displaceably in a sleeve 60 of the jaw part holder 30. Here, the sleeve 60 is guided in a channel 62 in the interior of the shaft 12.

In the embodiment shown here, the channel 62 is formed in a feed element 64 in which the longitudinal groove 50 is also formed. This will be illustrated again in FIG. 6 with reference to a further exemplary embodiment.

Finally, FIG. 4 also shows a terminating element 66 in which the annular groove 54 is formed. In this embodiment, the stop 56 is also formed on the terminating element 66.

Figure 5:
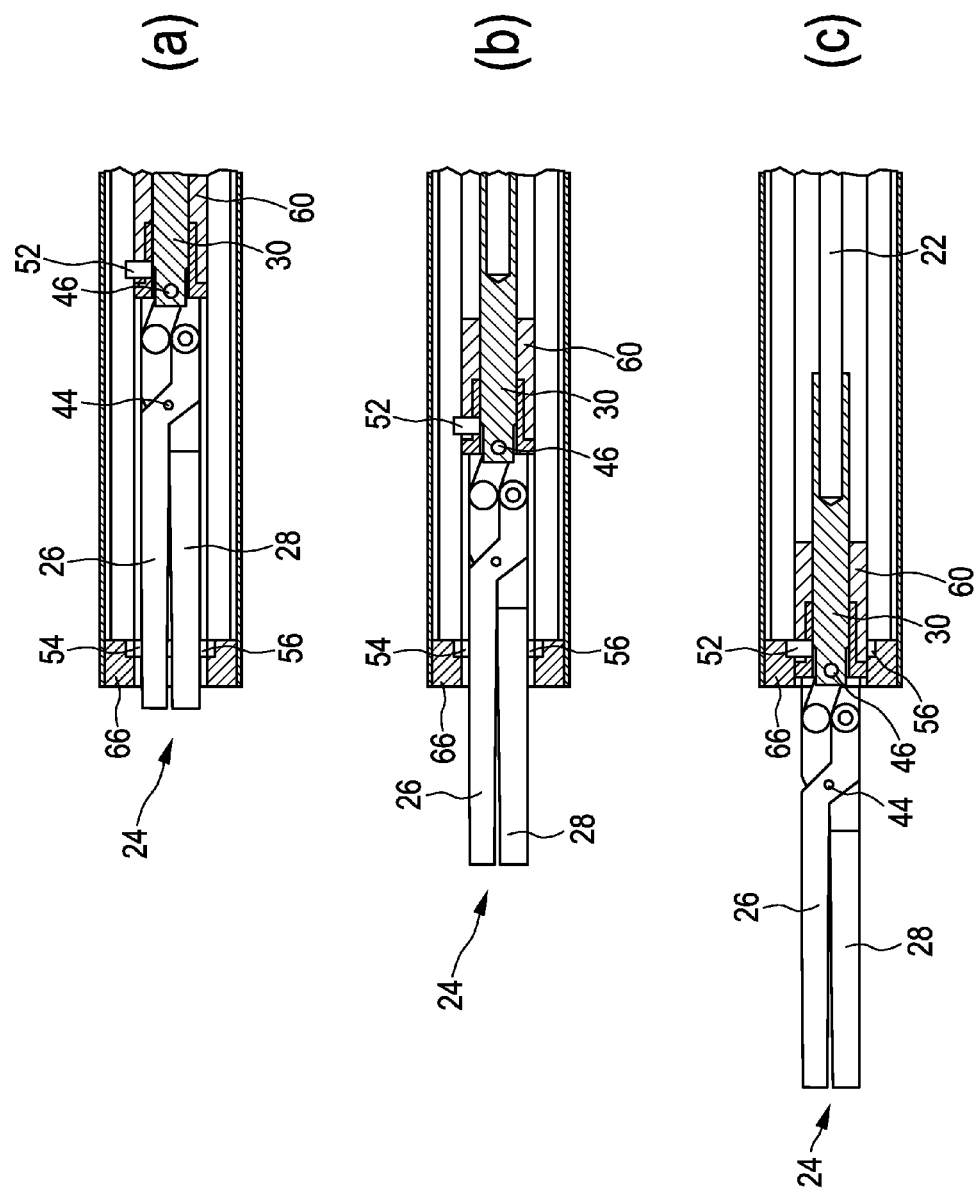
FIG. 5 shows simplified views of the interior of the distal part of the endoscopic instrument, with the closed jaw piece in different positions.

FIG. 5 is an illustration of the jaw piece 24 in different positions relative to the shaft 12. In this case, part (a) shows the retracted state of the jaw piece 24, and part (b) shows the partially deployed state of the jaw piece 24. Finally, part (c)

shows the fully deployed state of the jaw piece 24, wherein the projection 52 has passed from the longitudinal groove 50 into the annular groove 54 and the stop 56 prevents a further displacement of the jaw part holder 30 distally.

In this exemplary embodiment, the configuration of the shaft 12, more precisely of the feed element 64, is selected such that the jaw piece 24 cannot open when in the shaft. When subjected to a thrust action, the thrust element 22 duly transmits to the jaw piece 24 a force which could open the jaw piece 24. The shaft 12 is however configured, in spatial terms, such that an opening of the jaw piece 24 in the shaft 12 is prevented.

The following statements relate to a second embodiment of the endoscopic instrument 10, which may permit the use of two working sections. The explanations relating to the preceding embodiment with one working section can be transferred correspondingly to said second embodiment. Technical teachings which relate to one working section and which do not imperatively require the interaction of both working sections can also be transferred from the second embodiment to the first embodiment.

Figure 6:
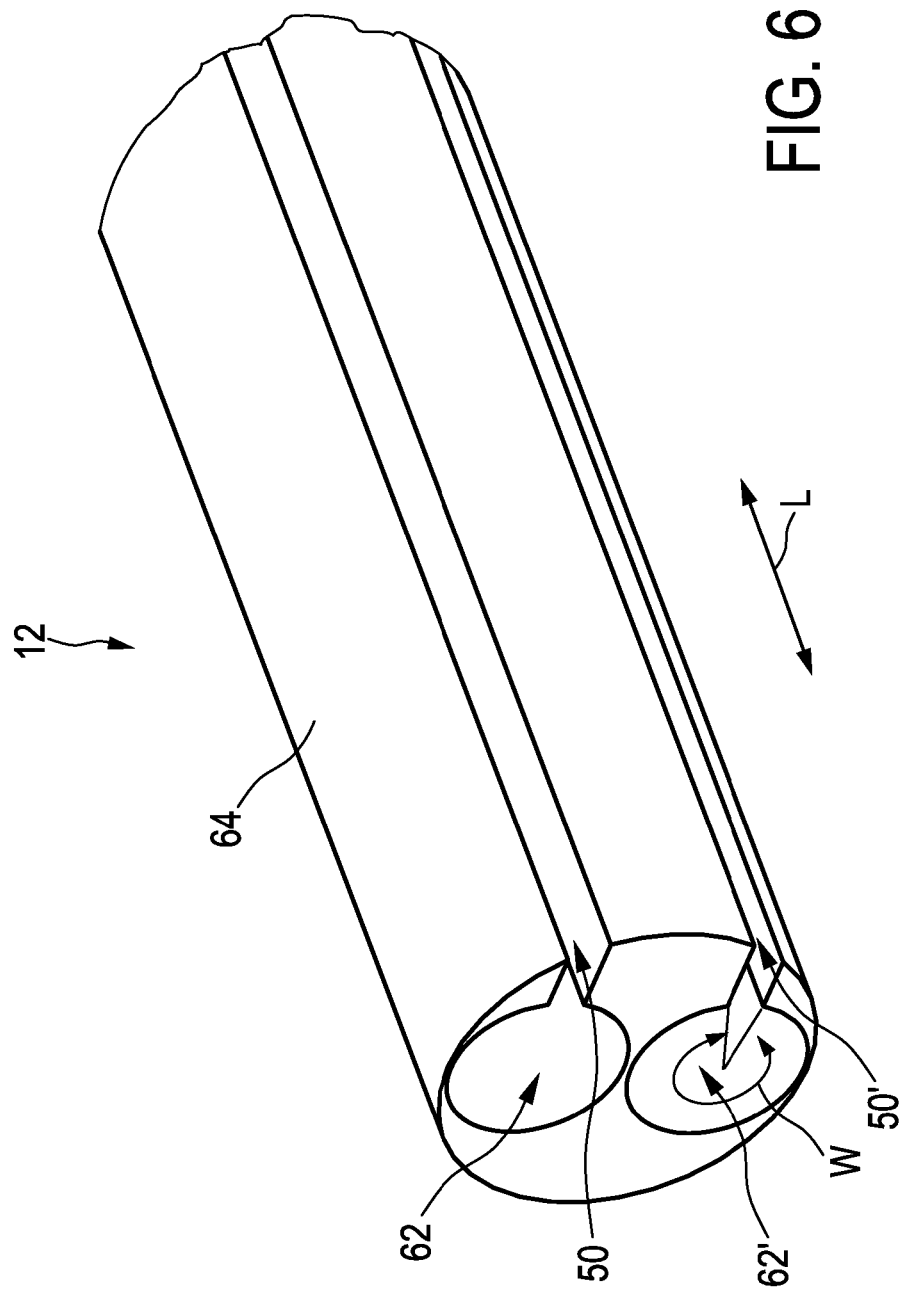
FIG. 6 shows a part of a shaft of an endoscopic instrument as per a second embodiment.

FIG. 6 shows a feed element 64 of an endoscopic instrument 10 as per a second embodiment. The feed element 64 has a first channel 62 and a second channel 62'. A first longitudinal groove 50 is formed on the first channel 62, and a second longitudinal groove 50' is formed on the second channel 62'. Here, the longitudinal grooves 50, 50' are formed all the way to the periphery of the feed element 64. This refinement facilitates the production of the feed element 64, though it may also possible be for the longitudinal grooves 50, 50' to be formed with a smaller depth proceeding from the respective channel 62, 62', such that the longitudinal grooves 50, 50' do not reach the cylinder surface of the feed element 64, and the cylinder surface is closed.

This view also illustrates the angle range W in which a retraction of the jaw piece 24 is blocked. For the actuation of the jaw piece, according to an exemplary embodiment, use is made here of a slotted guide from WO 2007/144172 A1, the document incorporated by reference in its entirety.

Figure 7:
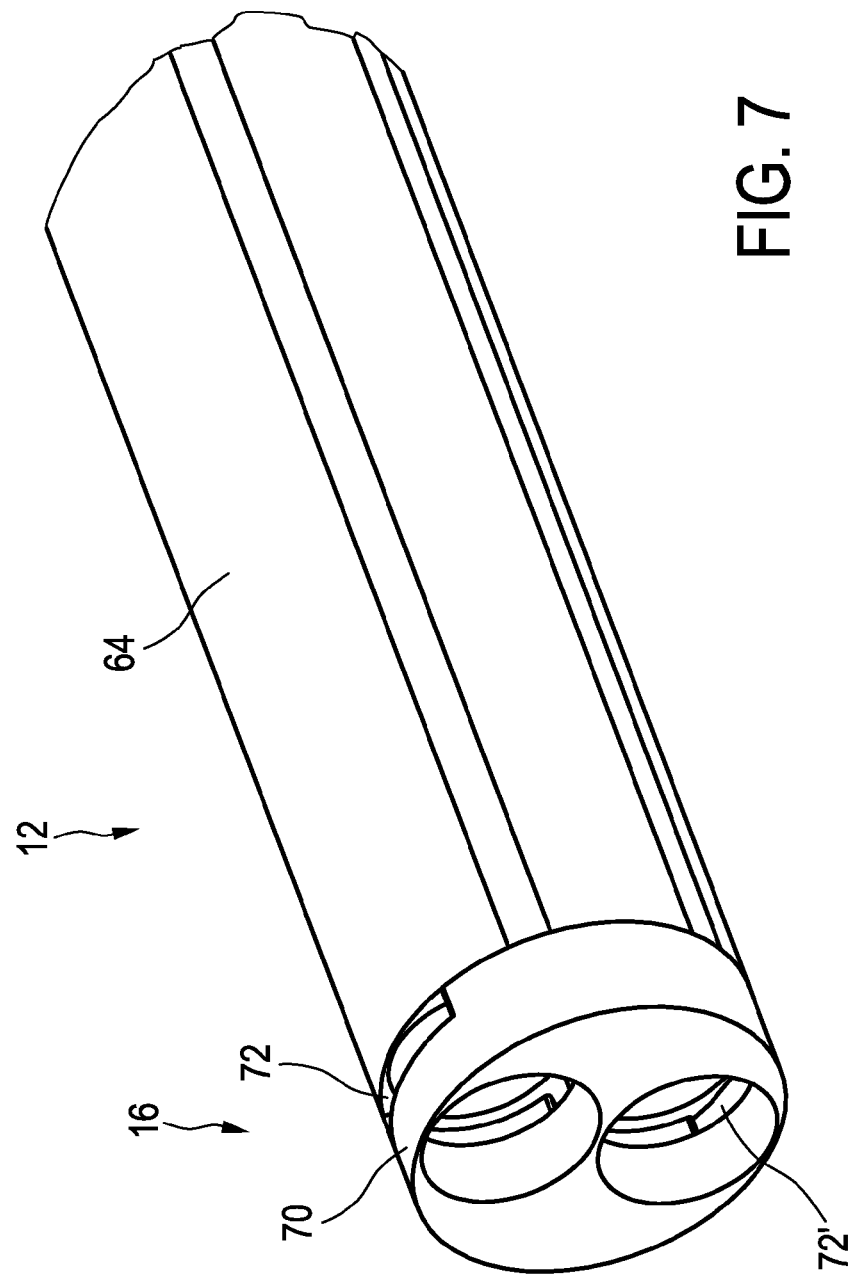
FIG. 7 shows the illustration from FIG. 6 with a terminating element mounted thereon.

FIG. 7 shows the feed element 64 as per FIG. 6 with a terminating element 70 which, by contrast to the terminating element 66 from FIG. 5, has two openings. The terminating element 70 is illustrated in yet more detail in FIGS. 14 and 15. It is however already evident here that the shaft 12 has, on the distal end 16, a first opening slot 72 and a second opening slot 72' into which a projection 52 of the blocking device 32 can enter during a rotation about the longitudinal direction L.

Figure 8:
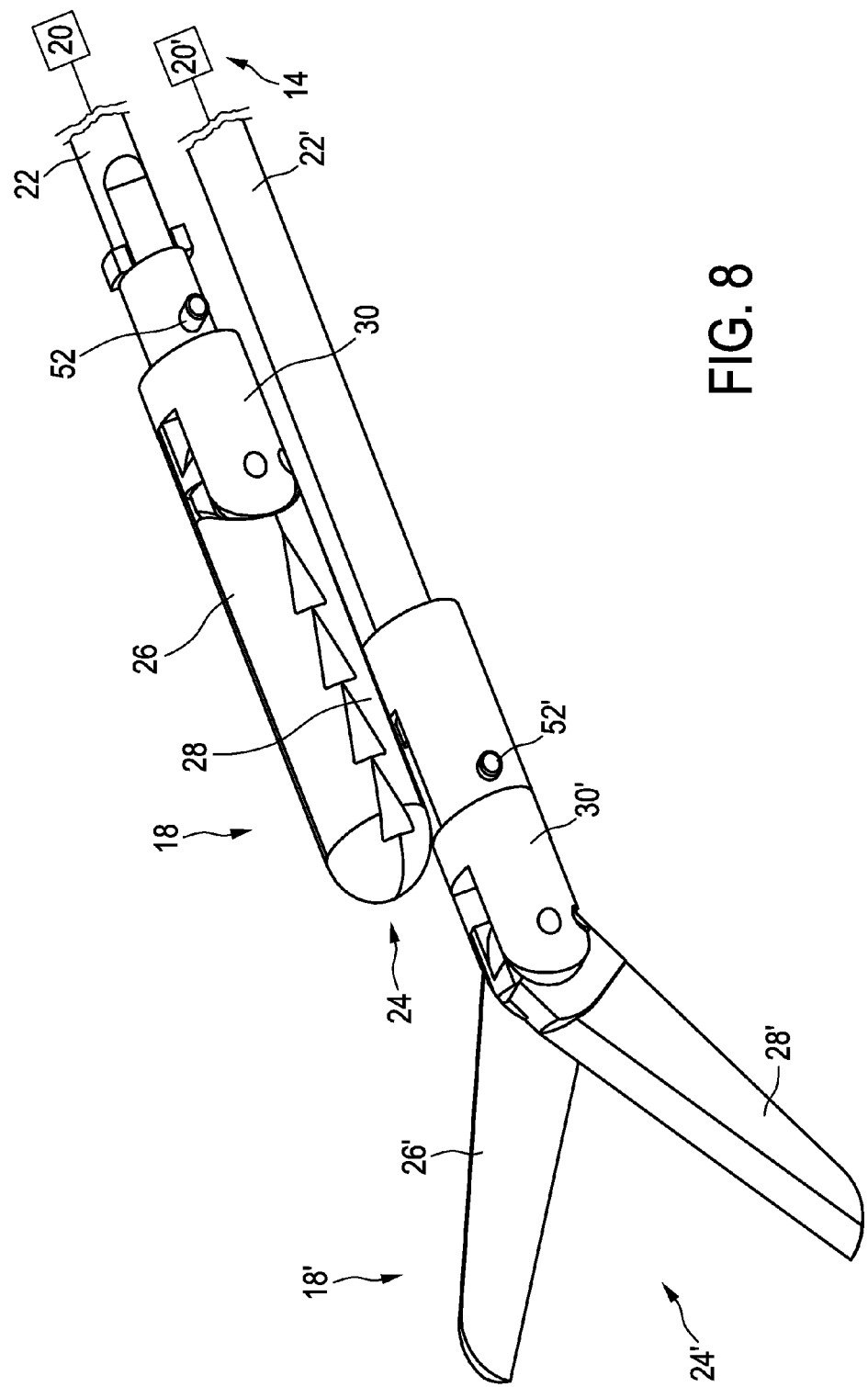
FIG. 8 shows the arrangement of two working sections, in an isolated illustration.

FIG. 8 shows, in an isolated illustration, that a second working section 18' is provided in addition to the first working section 18'. Furthermore, on the proximal end, there is arranged a second actuating element 20' in addition to the first actuating element 20. The second actuating element 20' permits an actuation of the second working section 18'. The second working section 18' is operatively connected to the second actuating element 20' by way of a second thrust element 22' which extends along the longitudinal direction L. The second working section 18' has a second jaw piece 24' with a third jaw part 26' and with a fourth jaw part 28'. The second jaw piece 24' is pivotably arranged on a second jaw part holder 30'. The second jaw part holder 30' is arranged in the shaft 12 (see FIG. 9) so as to be displaceable along the longitudinal direction L and rotatable about the longitudinal direction L.

The second thrust element 22' is coupled to the second jaw piece 24'. The second jaw piece 24' is configured such that, in the closed state, it can be retracted into the shaft 12, in particular into the second channel 62' of the feed element 64 (see FIG. 6). Within the instrument 10, there is arranged a second blocking device 32' which is configured to block a retraction of the second jaw piece 24' into the shaft 12 in a second angle range W' about the longitudinal direction L. The explanations given with regard to the first angle range W also apply to the second angle range W'. In this refinement, the angle ranges are selected to be equal. In further exemplary embodiments, they may however differ.

Figure 9:
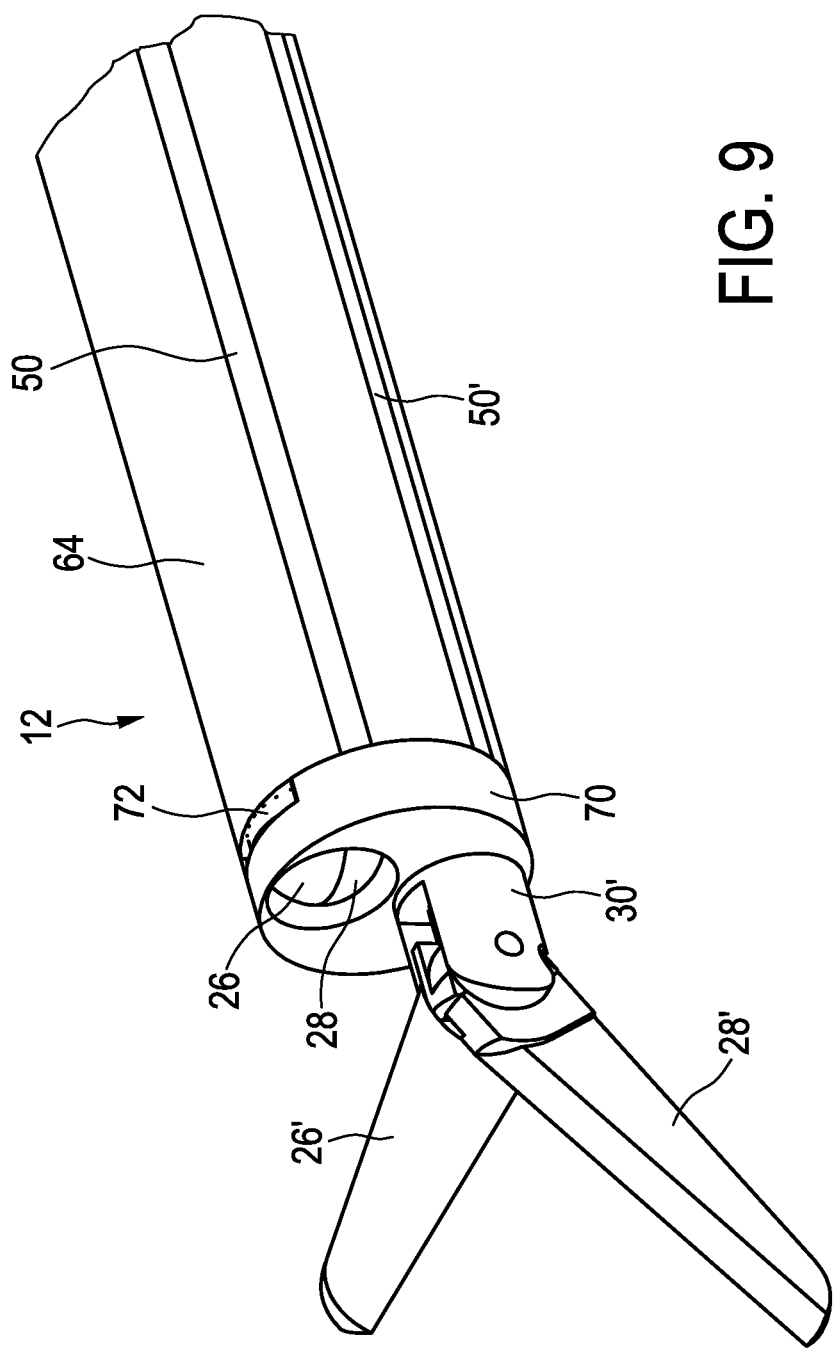
FIG. 9 shows the working sections from FIG. 8, inserted into the shaft with terminating element as per FIG. 7.

FIG. 9 shows the way in which the working sections from FIG. 8 are installed in the construction as per FIG. 7.

Figure 10:
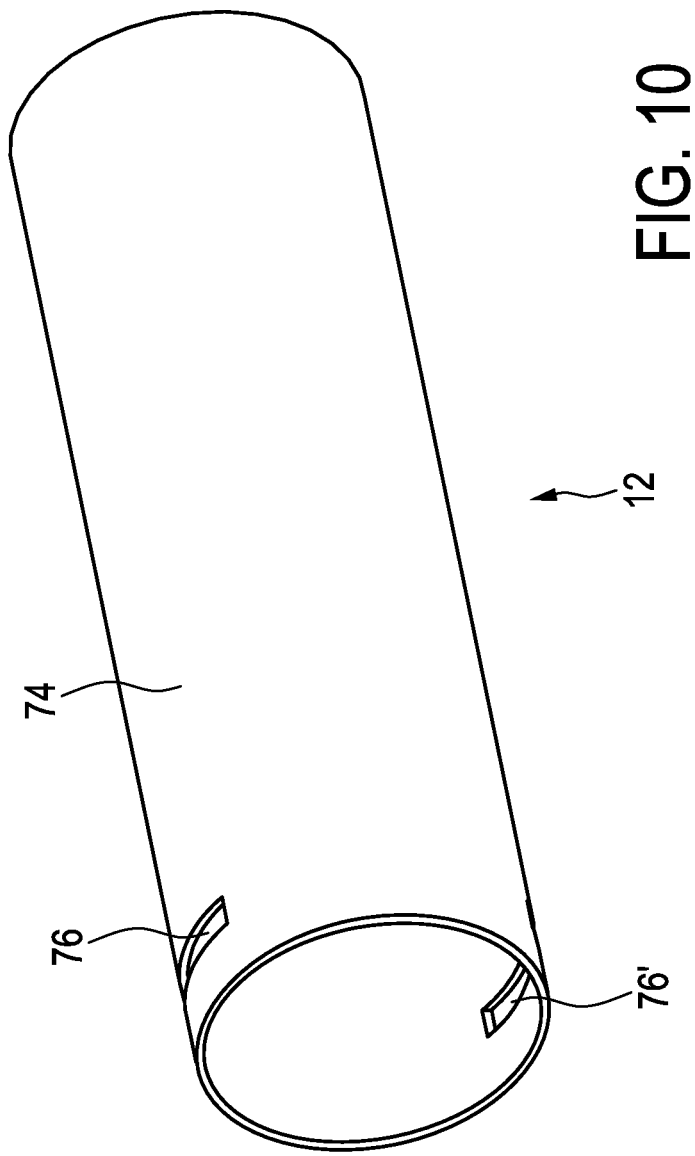
FIG. 10 shows a casing of the shaft as per FIG. 7.

FIG. 10 shows a casing 74 of the shaft 12. In this case, too, opening slots 76, 76' are formed which correspond to the opening slots 72, 72' and which also allow a projection 52 to enter them. The casing 74 serves for improved manufacturability and usability, and is not imperatively necessary.

Figure 11:
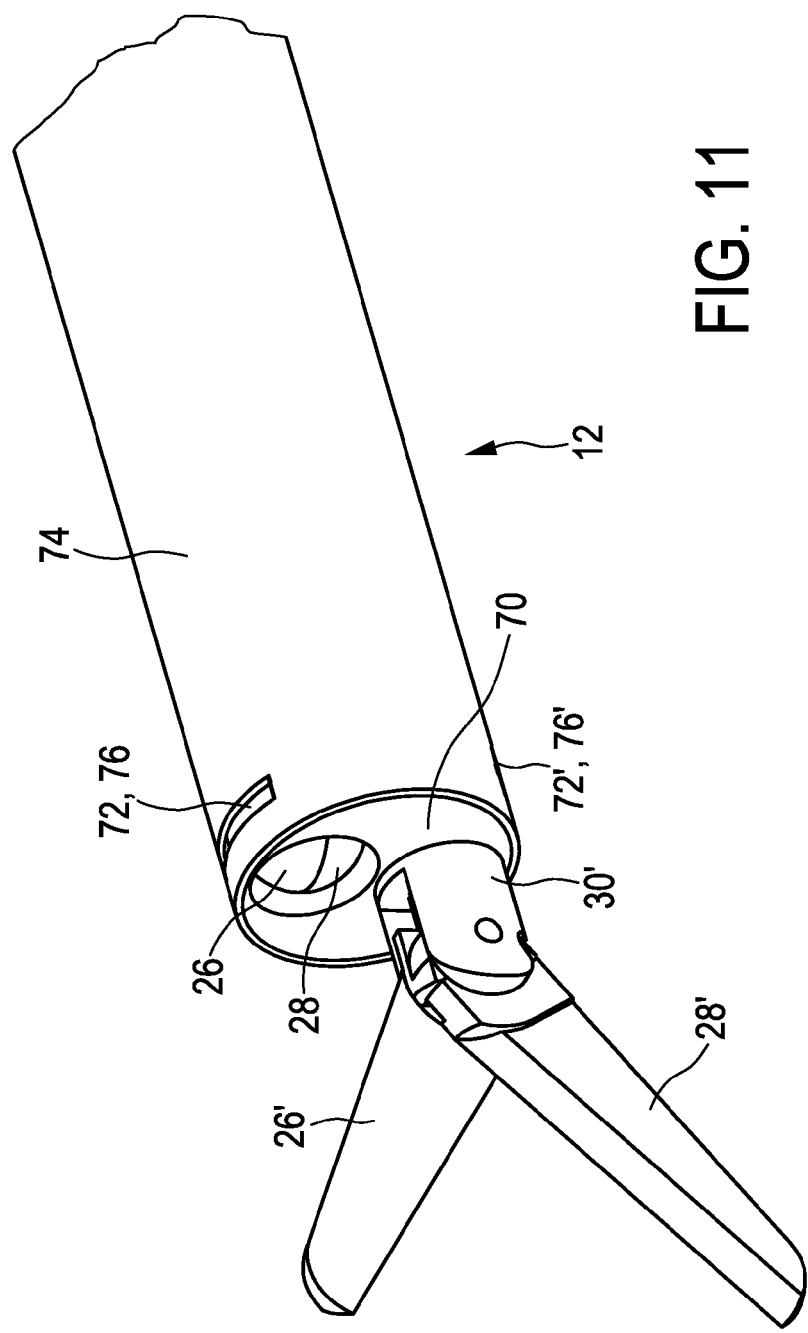
FIG. 11 is an illustration as per FIG. 9 with the casing from FIG. 10.

FIG. 11 shows the illustration from FIG. 9 with the casing 74 as per FIG. 10 in a mounted position.

Figure 12:
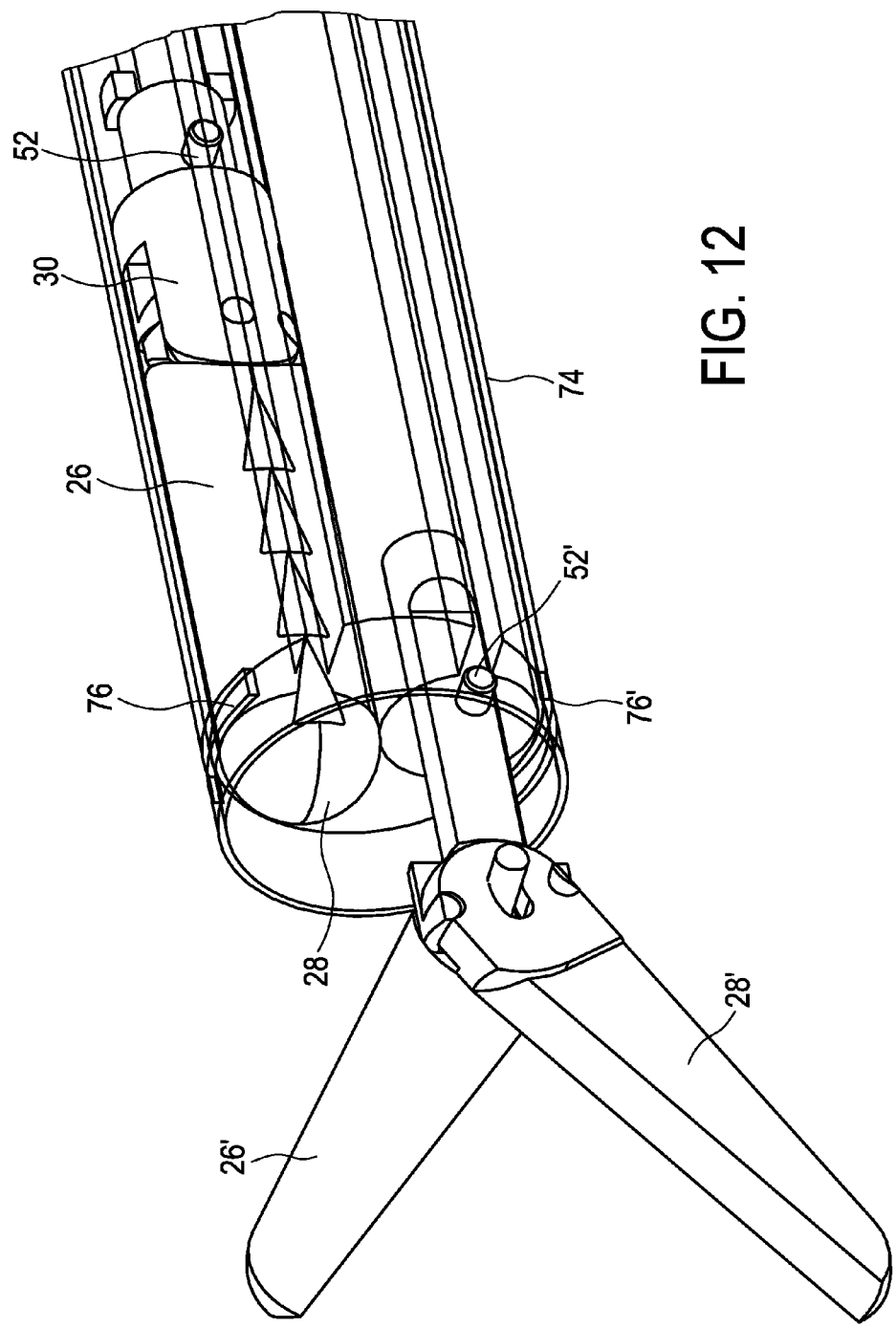
FIG. 12 is the illustration from FIG. 11, with the shaft, the terminating element and the casing illustrated in transparent form.

FIG. 12 is a partially transparent illustration of FIG. 11, with the terminating element 66 not shown.

Figure 13:
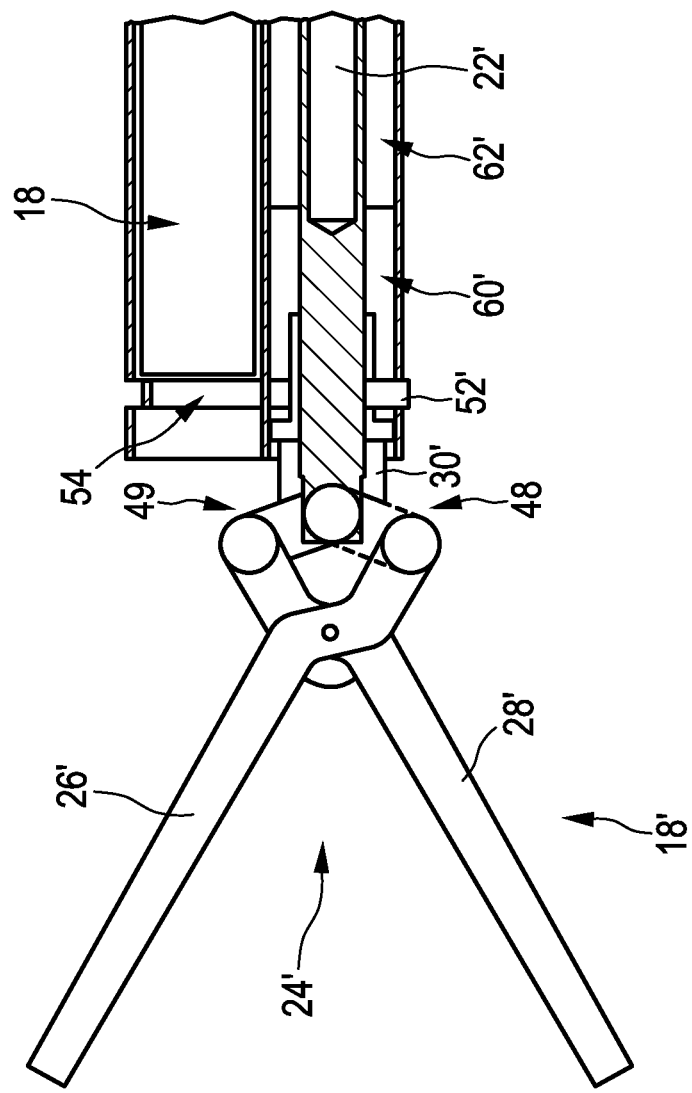
FIG. 13 shows a view into the interior of the distal part of the endoscopic instrument as per the second embodiment.

FIG. 13 shows a simplified view of the interior of the distal part of the second embodiment. It can be seen here that the second projection 52' has partially emerged through the opening slots 72', 76'.

It can be seen that a displacement of the second thrust element 22' in the longitudinal direction L now opens or closes the jaw piece 24'. In the illustration shown, a displacement of the second jaw part holder 30' is not possible because the second projection 52' does not correspond with the second longitudinal groove 50'. If the second jaw part holder 30' is rotated by the second thrust element 22' such that the second projection 52' corresponds with the second longitudinal groove 50', a pulling action on the thrust element 22' causes a closure of the second jaw piece 24' and ultimately a retraction of the second jaw piece 24'.

Figure 14:
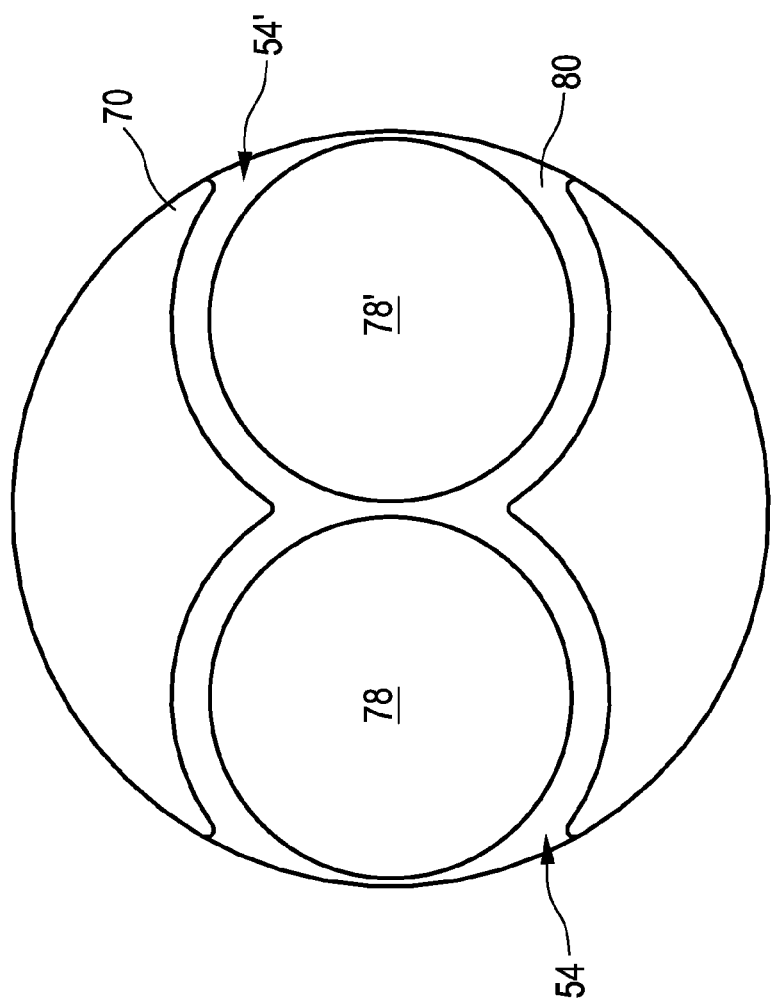
FIG. 14 shows a plan view of the terminating element, viewed in a direction toward the distal end.

FIG. 14 shows a first embodiment of the terminating element 70. It is possible to see the openings 78 and 78' for the first and second working sections 18, 18' respectively. Also shown is a recessed region 80 which forms the annular groove 54 and 54' for the projection 52 and 52' respectively.

Figure 15:
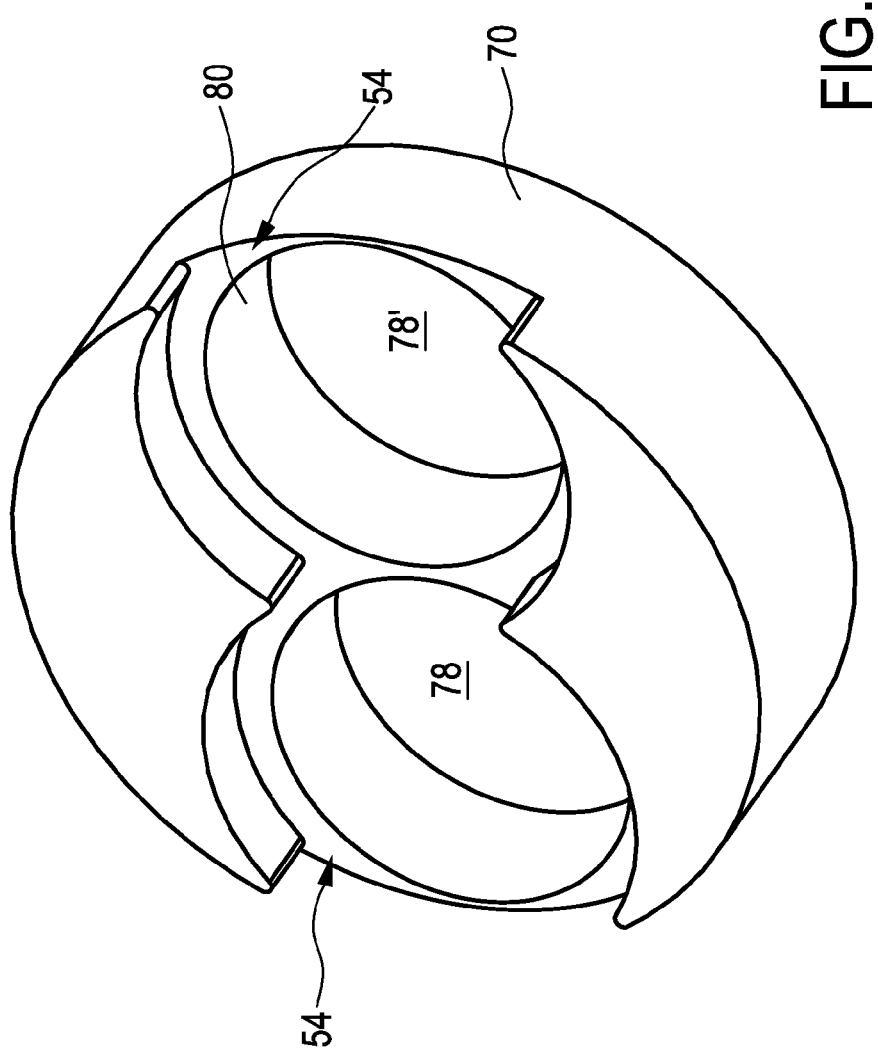
FIG. 15 is a perspective illustration of the terminating element as per FIG. 14.

FIG. 15 shows the terminating element 70 in a perspective illustration.

Figure 16:
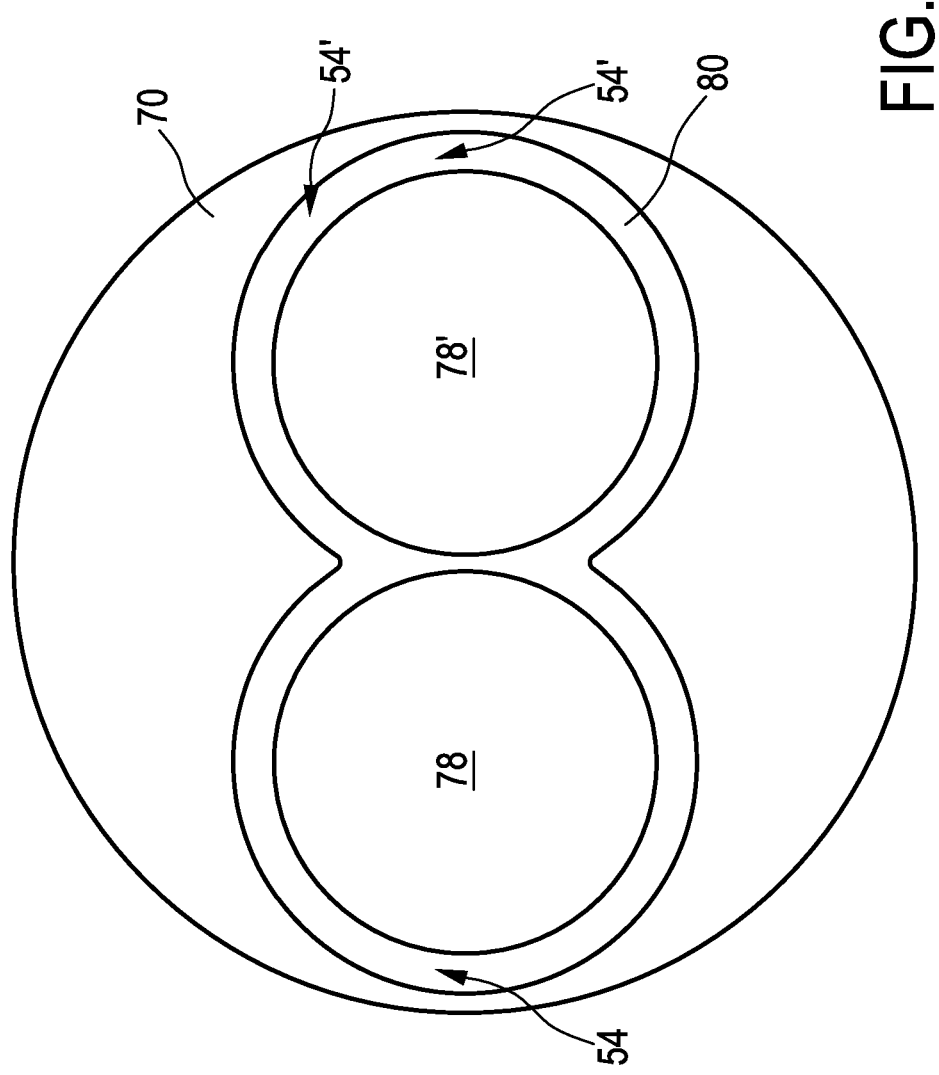
FIG. 16 shows a further embodiment of the terminating element.

FIG. 16 shows a second embodiment of a terminating element 70. By contrast to FIG. 14, the dimensions have in this case been selected such that the openings 78, 78' have the same diameter, but the terminating element 70 as a whole has a greater diameter. This may make it possible for the projections 52, 52' to be guided entirely within the shaft 12, and for at least the external opening slots 76, 76' to be omitted.

An endoscopic instrument 10 has been presented which, even in the case of a small diameter and large length of the shaft, may permit a wide variety of possible movements of the working section on the distal end of the instrument.

What is claimed is:

1. An endoscopic instrument comprising a shaft which extends between a proximal end of the instrument and a distal end of the instrument along a longitudinal direction, wherein a working section is arranged on the distal end and an actuating element is arranged on the proximal end, which actuating element permits an actuation of the working section, wherein the working section and the actuating element are operatively connected by a thrust element which extends along the longitudinal direction, wherein the working section has a jaw piece with a first jaw part and a second jaw part, which jaw piece is arranged pivotably on a jaw part holder, wherein the jaw part holder is arranged in the shaft so as to be displaceable along the longitudinal direction and rotatable about the longitudinal direction and the thrust element is coupled to the jaw piece, wherein the jaw piece is configured such that, in a closed state, the jaw piece can be retracted into the shaft, wherein, in the instrument, there is provided a blocking device which is configured to block a retraction of the jaw piece into the shaft in a predefined angle range about the longitudinal direction, wherein the blocking device has a first blocking element, which is arranged positionally fixedly relative to the shaft, and a second blocking element, which is arranged positionally fixedly relative to the jaw part holder, and wherein the first blocking element is in the form of a groove, and the second blocking element is in the form of a projection.

2. The endoscopic instrument of claim 1, wherein the groove of the first blocking element is a longitudinal groove, which is formed in the shaft along the longitudinal direction, and the projection of the second blocking element is guided in the longitudinal groove during a displacement of the jaw part holder along the longitudinal direction.

3. The endoscopic instrument of claim 1, wherein, on the distal end of the shaft, there is formed an annular groove into which the projection of the second blocking element can enter, such that the jaw part holder can be rotated about the longitudinal direction when the projection has entered the annular groove.

4. The endoscopic instrument of claim 1, wherein the groove of the first blocking element is a longitudinal groove, which is formed in the shaft along the longitudinal direction, and the projection of the second blocking element is guided in the longitudinal groove and in an annular groove on the distal end of the shaft.

5. The endoscopic instrument of claim 1, wherein the first jaw part and the second jaw part are pivotable about a common first axis and the jaw piece is coupled to the thrust element at a second axis, wherein the first axis and the second axis are spaced apart from one another.

6. The endoscopic instrument of claim 5, wherein the first axis is situated further distally than the second axis.

7. The endoscopic instrument of claim 1, wherein the first jaw part is coupled to the thrust element by way of a first articulated connection and/or the second jaw part is coupled to the thrust element by way of a second articulated connection.

8. The endoscopic instrument of claim 1, wherein, on the distal end of the shaft, there is formed a stop which delimits a displacement of the jaw part holder along the longitudinal direction at a distal side.

9. The endoscopic instrument of claim 1, wherein the thrust element is displaceable along the longitudinal direction relative to the jaw part holder at least when the jaw piece has been deployed out of the shaft.

10. The endoscopic instrument of claim 1, wherein the thrust element, when subjected to a thrust action toward the distal end, exerts on the jaw piece a force which can open the jaw piece, and the shaft is configured such that an opening of the jaw piece in the shaft is prevented.

11. The endoscopic instrument of claim 1, wherein the thrust element has an elongate thrust shaft which is guided displaceably in a sleeve of the jaw part holder, wherein the sleeve is guided in a channel in an interior of the shaft.

12. The endoscopic instrument of claim 1, wherein the shaft has, at the distal end, a region which can be angularly deflected, and the angular deflection is controlled by an angular-deflection control element which can be actuated from the proximal end of the instrument.

13. The endoscopic instrument of claim 1, wherein a second working section is arranged on the distal end and a second actuating element is arranged on the proximal end, which second actuating element permits an actuation of the second working section, wherein the second working section and the second actuating element are operatively connected by way of a second thrust element which extends along the longitudinal direction, wherein the second working section has a second jaw piece with a third jaw part and with a fourth jaw part, which second jaw piece is pivotably arranged on a second jaw part holder, wherein the second jaw part holder is arranged in the shaft so as to be displaceable along the longitudinal direction and rotatable about the longitudinal direction, and the second thrust element is coupled to the second jaw piece, wherein the second jaw piece is configured such that, in the closed state, it can be retracted into the shaft, wherein, within the instrument, there is arranged a second blocking device which is configured to block a retraction of the second jaw piece into the shaft in a second angle range about the longitudinal direction.

14. The endoscopic instrument of claim 1, wherein the shaft has, on the distal end, an opening slot into which the projection of the blocking device can enter during a rotation about the longitudinal direction.

15. The endoscopic instrument of claim 1, wherein the angle range is at least 180°.

16. The endoscopic instrument of claim 1, wherein the angle range is at least 335°.

17. An endoscopic instrument comprising a shaft which extends between a proximal end of the instrument and a distal end of the instrument along a longitudinal direction, wherein a working section is arranged on the distal end and an actuating element is arranged on the proximal end, which actuating element permits an actuation of the working section, wherein the working section and the actuating element are operatively connected by a thrust element which extends along the longitudinal direction, wherein the working section has a jaw piece with a first jaw part and a second jaw part, which jaw piece is arranged pivotably on a jaw part holder, wherein the jaw part holder is arranged in the shaft so as to be displaceable along the longitudinal direction and rotatable about the longitudinal direction and the thrust element is coupled to the jaw piece, wherein the jaw piece is configured such that, in the closed state, the jaw piece can be retracted into the shaft, wherein, in the instrument, there is provided a blocking device which is configured to block a retraction of the jaw piece into the shaft in a predefined angle range about the longitudinal direction, wherein the blocking device has a first blocking element, which is arranged positionally fixedly relative to the shaft, and a second blocking element, which is arranged positionally fixedly relative to the jaw part holder, and wherein the first blocking element is in the form of a projection, and the second blocking element is in the form of a groove.

* * * * *